United States Patent
Frot

(10) Patent No.: US 7,199,871 B2
(45) Date of Patent: Apr. 3, 2007

(54) REFRACTOMETER AND METHOD FOR MEASURING REFRACTIVE INDEX

(75) Inventor: Didier Frot, Germain-en-Laye (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 385 days.

(21) Appl. No.: 10/478,507

(22) PCT Filed: May 3, 2002

(86) PCT No.: PCT/FR02/01528

§ 371 (c)(1),
(2), (4) Date: Nov. 24, 2003

(87) PCT Pub. No.: WO02/095374

PCT Pub. Date: Nov. 28, 2002

(65) Prior Publication Data

US 2004/0130706 A1    Jul. 8, 2004

(30) Foreign Application Priority Data

May 23, 2001   (FR)   ................................. 01 06866

(51) Int. Cl.
*G01N 21/41* (2006.01)
(52) U.S. Cl. ...................... 356/128; 356/133
(58) Field of Classification Search ......... 356/128–137
See application file for complete search history.

(56) References Cited

U.S. PATENT DOCUMENTS

| 3,650,631 A | | 3/1972 | Grässel et al. | |
|---|---|---|---|---|
| 4,451,147 A | * | 5/1984 | Dobes et al. | ............... 356/135 |
| 5,946,096 A | * | 8/1999 | Lee et al. | .................... 356/484 |
| 5,956,132 A | * | 9/1999 | Donzier | ...................... 356/133 |
| 6,304,328 B1 | * | 10/2001 | Longtin | ...................... 356/445 |
| 6,975,388 B2 | * | 12/2005 | Frot | ........................... 356/128 |

FOREIGN PATENT DOCUMENTS

| EP | 0 043 522 A1 | 6/1981 |
| EP | 0 071 143 A1 | 2/1983 |
| FR | 2 578 978 | 9/1986 |
| FR | 2 725 788 | 4/1996 |
| WO | WO 82/03460 | * 10/1982 |

* cited by examiner

*Primary Examiner*—Hoa Q. Pham
(74) *Attorney, Agent, or Firm*—Antonelli, Terry, Stout and Kraus, LLP.

(57) ABSTRACT

The invention relates to a refractometer and to a refractive index measuring method. The invention directs an incident light ray onto an interface of a medium of known refractive index and of the medium studied, then measuring the intensity of the reflected light ray. The ratio between the intensity of the incident ray and the intensity of the reflected ray allows the refractive index of the medium studied to be calculated by means of Fresnel's formulas.

9 Claims, 2 Drawing Sheets

REFRACTOMETER AND METHOD FOR MEASURING REFRACTIVE INDEX

BACKGROUND OF THE INVENTION

1. Field of the Invention

The present invention relates to determination of the refractive index of a medium and provides a method and a refractometer for absolute measurement of the refractive index.

2. Description of the Prior Art

Current methods of determining the refractive index of a medium are based on Descartes' laws describing the refraction phenomenon of passage of a light ray through an interface between the medium to be studied and a medium of known refractive index. These methods generally measure characteristics of the ray refracted by the interface to determine the refractive index of the medium being studied. More particularly, some methods exploit the existence of a limit angle of refraction. These methods determine the angle of an incident ray for which reflection is total and refraction non-existent. This angle corresponds to what is referred to as critical angle.

The refractometers measuring characteristics of a refracted ray or of the critical angle can be classified into two instrument categories.

On the one hand, there are refractometers performing absolute measurement of the refractive index. These tools allow, among other things, to control the quality of a product, to identify a component or to determine the proportions of the various components of a mixture. They are commonly used in the chemical, pharmaceutical and food-processing industry, and in analysis laboratories.

On the other hand, there are refractometers performing differential refractive index measurement between two media. The most widely known application of this category of instruments is analysis of the composition of a liquid solution after separation, by chromatography, of the different components upon passage of the liquid solution on an adsorbent solid.

EP-043,667 describes a refractometer using the comparison between the intensity of a first reflected ray and the intensity of a second reflected ray. The intensity of the first reflected ray depends on the refractive index of the medium being studied, whereas the intensity of the second reflected ray is independent of the refractive index of the medium studied. However, the intensity value of the second ray is totally independent of the intensity of the first ray. Intensity measurement of two different light rays notably has the drawback of following a complex procedure for measuring a refractive index and of losing measuring precision.

U.S. Pat. No. 3,650,631 describes a refractometer using the comparison between a first reflected ray and the intensity of a second ray reflected on an interface between the medium studied and a reference solid. The first ray falls onto the interface with an angle of incidence which is smaller than the critical angle, and the second ray falls onto the interface with an angle of incidence larger than the critical angle. The refractometer described in the '631 patent requires a critical angle. Now, the critical angle is determined by the refractive indices of the media that constitute the interface. This requirement therefore imposes limitations on the refractive index value measurable by the refractometer of the '631 patent. Furthermore, determination of the refractive index is based on the measurement of the intensity of the second ray which undergoes a total reflection at the interface. Now, in total reflection (angle of incidence larger than the critical angle), the evanescent wave appears, i.e. a phenomenon where the incident ray of the reference medium passes into the medium to be studied before it is reflected in the reference medium. In case of a highly absorbent studied medium, the intensity of the second reflected ray is attenuated and determination of the refractive index loses precision.

However, several limitations of use exist for refractometers measuring characteristics of the refracted light ray or the critical angle.

One limitation concerns the restricted measuring range of the refractive index of the medium studied. An absolute-measuring refractometer generally scans a range between approximately 1.3 and 1.7 RIU (Refractive Index Unit) for liquid media and between approximately 1.1 and 1.2 RIU for gaseous media, with a sensitivity of about $10^{-4}$ RIU. The measuring range of a differential-measuring refractometer extends approximately over $10^{-3}$ RIU with a sensitivity of $10^{-7}$ RIU.

Furthermore, measurement based on the characteristic of the refracted ray prevents determination of the refractive index of an opaque medium because the refracted ray is absorbed by the opaque medium. By determining the angle from which reflection is total, the evanescent wave (a phenomenon which causes passage of the incident ray at an interface from the first medium into the second medium before it is reflected in the first medium) is also absorbed by the second medium if it is opaque. Thus, measurement of the refractive index of media such as, for example, crude petroleum, inks and paints is not possible with such instruments.

Moreover, determination of the refractive index of a flowing fluid can be imprecise. In fact, if the fluid has no homogeneous optical characteristics as a result of its flow, the refracted ray or the evanescent wave propagated in the fluid undergoes alterations. The changes in the characteristics of the refracted ray or of the evanescent wave become greater when the flow of the fluid is turbulent.

For the same reasons as with determination of the refractive index of a flowing fluid, determination of the refractive index of a dispersed medium can be imprecise because dispersed media have no homogeneous optical characteristics.

The present invention provides a method and a refractometer allowing absolute measurement of a refractive index and overcoming the limitations of the prior art.

SUMMARY OF THE INVENTION

The invention directs an incident light ray onto an interface between a medium of known refractive index and of the medium being studied, then in measuring the intensity of the reflected light ray. The ratio between the intensity of the incident ray and the intensity of the reflected ray allows the refractive index of the medium being studied to be calculated by means of Fresnel's formulas.

Determination of the refractive index of a medium has many applications, notably recognition of a compound and/or of the composition of a mixture, quality control in industrial production.

In the present description, the refractive index of a medium is the ratio of the propagation velocity of light in a vacuum divided by the propagation velocity of light in this medium.

Light rays are electromagnetic waves with wavelengths in the ultraviolet, visible and infrared frequency ranges extending to the radio frequency range.

The intensity of a light ray is the flux of photons traversing a surface for a given time.

One of the difficulties linked with measurement of the intensity of the reflected light ray results from low intensity.

The invention relates to a method for measuring the refractive index of a first medium, comprising the following stages:

directing an incident light ray onto a first interface between the first medium and a second medium of known refractive index so as to produce a reflected light ray;

measuring the intensity of the incident light ray and the intensity of the reflected light ray; and determining the refractive index of the first medium by accounting for at least the refractive index of the second medium, the intensity of the incident light ray and the intensity of the reflected light ray.

The refractive index of the first medium can be determined by means of a formula which relates the intensity of the incident light ray to the intensity of the reflected light ray at the first interface by accounting for the refractive index of the first medium and of the refractive index of the second medium, for example Fresnel's formulas.

With the method of the invention, the incident light ray can be coded, for example, by varying the intensity of the incident light ray according to a periodic signal and/or by varying the mean intensity of the incident light ray according to a square-wave signal.

With the method of the invention, a source light ray can be divided so as to form a reference light ray and the incident light ray, for example by means of a second interface.

The ratio of the intensity of the reference light ray to the intensity of the incident light ray can be determined using the first medium whose refractive index is known, by measuring the intensity of the reference light ray and the intensity of the reflected light ray and using a formula, for example Fresnel's formulas, which relates the intensity of the incident light ray to the intensity of the reflected light ray at the first interface by accounting for the refractive indices of the first medium and of the second medium.

In the method according to the invention, the intensity of the reference light ray can be measured to determine the intensity of the incident light ray.

In the method according to the invention, the intensity of the light ray refracted in the first medium is measured and the absorption in the first medium of the refracted light ray is determined.

In the method according to the invention, the angle of incidence of the incident light ray in relation to the normal direction to the first interface can be smaller than the critical angle and preferably below 10°.

The method according to the invention can be applied to measurement of the refractive index of an opaque medium such as, for example, crude petroleum.

The invention also relates to a refractometer comprising a light source, a first interface between a first medium of unknown index and of a second medium of known index and at least one detector measuring the intensity of an incident light ray and the intensity of a reflected light ray resulting from the reflection of the incident light ray on the first interface. The first medium can be contained in an enclosure of a shell and of the second medium.

The refractometer according to the invention comprises a means for coding the light ray emitted by the light source and a means for decoding measurements performed by the detector, the means for decoding exchanging information with the means for codes. The refractometer can also comprise an optical element, for example a second interface formed between the surface of the first medium located outside the enclosure or a semireflecting blade, suited to divide a light ray into two light rays so as to form a measuring ray and the incident ray, the intensity of the measuring ray being measured by a detector.

The refractometer according to the invention can comprise at least one detector measuring the intensity of a light ray refracted in the first medium.

According to the refractometer of the invention, the angle of incidence of the incident light ray in relation to the normal direction to the first interface can be smaller than the critical angle, preferably below 10°.

The method and the refractometer according to the invention notably have the advantage of providing a measuring range that can be included between 1 and 2.4 RIU for all media, in particular liquid and gaseous fluid media. Since the ray subjected to measurement does not pass through the medium being studied, in comparison with the refracted ray, or does not enter the medium being studied as much as the evanescent wave for an incident ray in the vicinity of the critical angle, it is possible to determine the refractive index of an opaque medium, of a flowing fluid medium or of a dispersed medium.

Direct measurement of the intensity of the incident ray and of the reflected ray simplifies the refractive index measuring procedure and improves the measuring accuracy. According to the present invention, the absolute refractive index can be obtained with a precision at least equal to $10^{-4}$ RIU.

The refractometer according to the invention requires no prior calibration, whether optical, mechanical or electric, before measurement.

According to the layout of the refractometer of the invention, the medium to be studied is separated from the remainder of the refractometer by an enclosure of the medium of known refractive index forming part of the interface and may be a shell. It is thus possible to measure the refractive index of a medium under pressure. Furthermore, by selecting a suitable material and geometry for the medium of known index and for the shell, the refractometer has a high mechanical and/or chemical strength. Besides, separation of the medium to be studied from the other elements of the refractometer facilitates maintenance of the device.

Furthermore, the refractometer according to the invention can be easily completed with means allowing measurement of the phenomenon of absorption of the medium studied.

BRIEF DESCRIPTION OF THE DRAWINGS

Other details, features and advantages of the invention will be clear from reading the description hereafter of an embodiment of the invention given by way of non limitative example, with reference to the accompanying figures wherein.

DETAILED DESCRIPTION OF THE INVENTION

Figure 1:
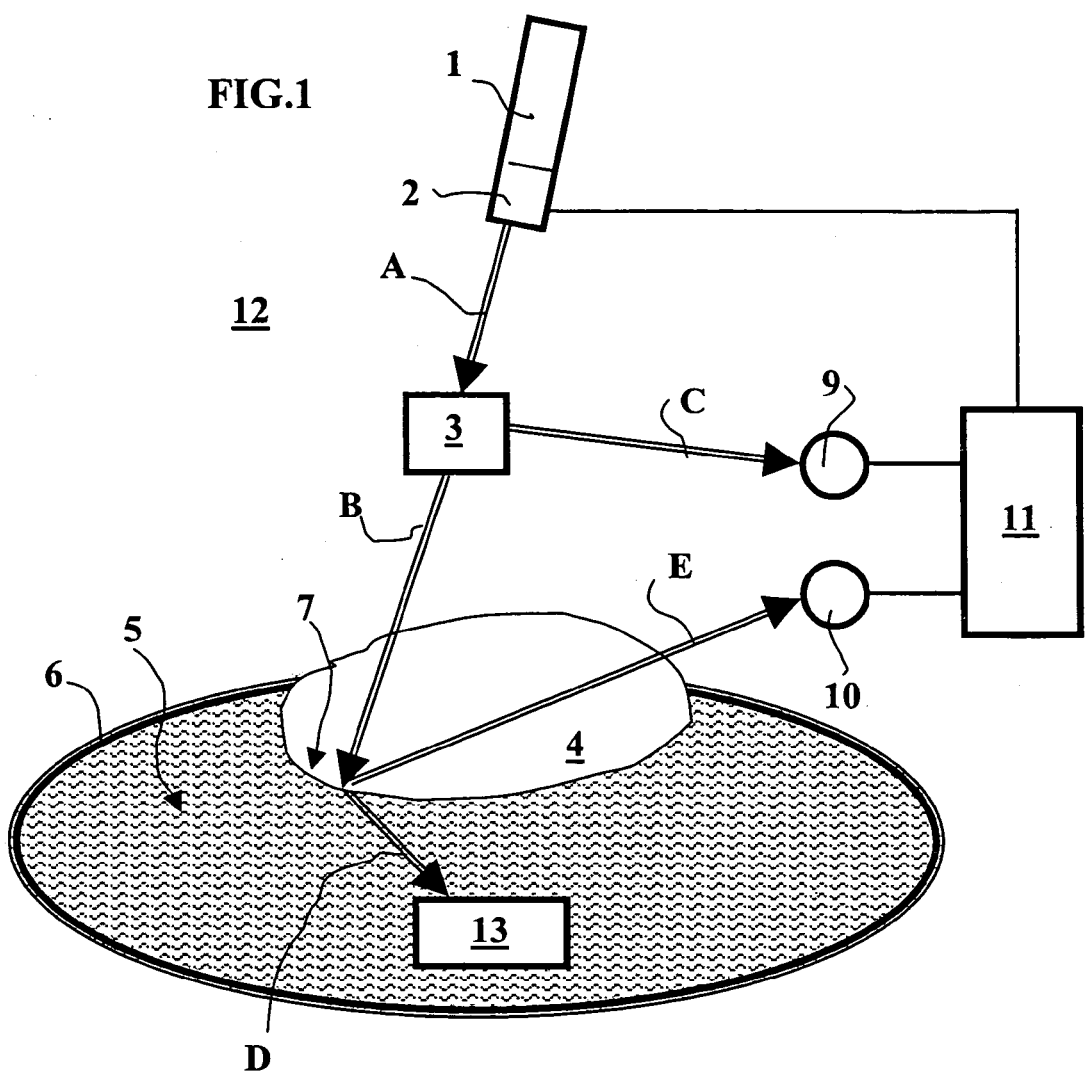
FIG. 1 shows the principle of a refractometer according to the invention.

According to the refractometer diagrammatically shown in FIG. 1, medium 5 of unknown refractive index is contained in an enclosure defined by shell 6. A window in its shell 6 is closed by a medium 4 of known refractive index. An ambient medium 12 of known refractive index is located outside the enclosure.

The enclosure can have various forms with the main purpose being to contain medium 5. Thus, the enclosure can be a pipe in which medium 5 circulates or an open or closed vessel. Since medium 5 can be under pressure and/or an active chemical agent, the enclosure is designed to withstand the mechanical and/or chemical stresses applied thereto by medium 5. Owing to its shape and to its material, medium 4 must have the same mechanical and chemical strength characteristics as shell 6.

The surface of medium 4 in contact with medium 5 forms an interface 7. Medium 4 is selected in such a way that it absorbs none or only a very small proportion of light, its refractive index is known with a precision of at least $10^{-4}$ RIU and the surface forming interface 7 produces no unwanted interference, diffusion or diffraction effects. Medium 4 can for example have the shape of a diamond porthole of refractive index 2.41 RIU.

Ambient medium 12 must have no effect on the light. It can be a controlled atmosphere or, more simply, of ambient air.

The refractometer comprises a light source 1. Light source 1 can emit a monochromatic light ray by means of a filter, for example, whose stability is $10^{-4}$ for the mean intensity emitted. It can be a laser diode or a laser emitting for example a ray whose intensity is about 5 mW. Coding device 2 codes the light ray emitted by source 1. Light source 1 and the coding device 2 are located in the ambient medium 12.

An optical element 3, located in ambient medium 12 between light source 1 and interface 7, divides an incident light ray into two light rays whose characteristics are identical to those of the incident light ray, but have different intensities. The sum of the intensities of the two rays from optical element 3 can be equal to the intensity of the incident ray. Optical element 3 can be a semireflecting blade or an interface.

Two photodetectors 9 and 10, which measure the intensity of a light ray, are located in ambient medium 12. Medium 5 comprises a photodetector 13 which measures the intensity of a light ray. Photodetector 13 is movable permitting variation of the distance separating the photodetector from the interface 7. It is also possible to maintain photodetector 13 outside medium 5 and to use a glass element transmitting a light ray from a first end of the element, located in the medium 5, to the second end of the element, outside medium 5. Photodetector 13 measures the intensity of the light ray coming from the second end of the glass element. The glass element, which is secured to photodetector 13, can be mobile. Furthermore, owing to the nature of it's material, the glass element does not modify the intensity value of the light ray which is transmitted therein.

A signal processor 11 is connected to the coding device 2 and to photodetectors 9, 10 and 13. These elements decode the signals picked up by photodetectors 9, 10 and 13 considering the coding performed by decoding device 2, and to compare and analyse the signals picked up by photodetectors 9, 10 and 13.

The refractometer can be provided with refrigeration in order to remove the heat coming notably from light source 1 which prevents modification of the value of the refractive index of medium 5 which varies by about $10^{-4}$ RIU per degree-C.°.

Light source 1, provided with the coding device 2, produces coded light ray A. Light ray A, after traversing ambient medium 12, enters optical element 3 where separation into two light rays B and C occurs.

Photodetector 9 measures the intensity of this light ray C.

At the outlet of optical element 3, light ray B propagates into ambient medium 12, then into medium 5 to interface 7 to produce a reflected light ray E and a refracted light ray D.

The intensity ID of light ray D refracted in medium 5 is measured by photodetector 13 in order to determine the transmission of medium 5. The direction of translation of photodetector 13 is selected preferably parallel to the direction of the light ray. The photodetector performs at least one measurement of intensity ID at a distance d (not illustrated) between photodetector 13 and interface 7. Photodetector 13 preferably performs at least three measurements of the intensity $ID_1$, $ID_2$ and $ID_3$ of ray D at respectively three distances $d_1$, $d_2$ and $d_3$ (not illustrated) between photodetector 13 and interface 7. If photodetector 13 is provided with a glass element, distances d, $d_1$, $d_2$ and $d_3$ correspond to the distance between interface 7 and the first end of the glass element because the glass element does not modify the intensity ID of ray D it picks up and transmits to photodetector 13.

Ray E is transmitted in medium 4, then exits and enters ambient medium 12. Photodetector 10 measures the intensity IE of this light ray E.

Figure 2:
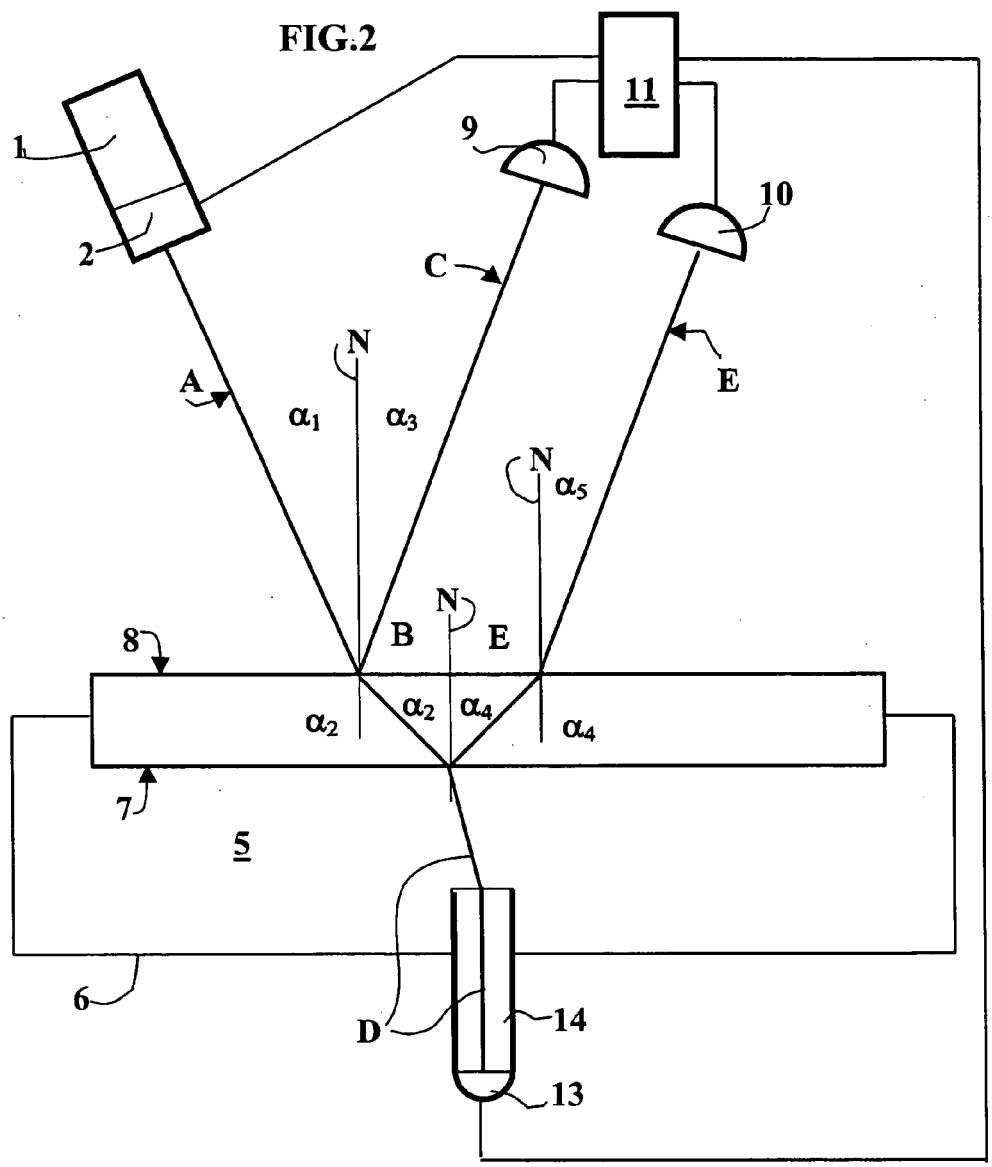
FIG. 2 diagrammatically shows a refractometer according to the invention.

FIG. 2 shows another embodiment of the refractometer according to the invention. The reference numbers in FIG. 2 which are identical to those of FIG. 1 designate the same elements. Light source 1, coding device 2, medium 4, medium 5, shell 6, interface 7, signal processor 11, medium 12, photodetectors 9, 10 and 13 can thus also be seen in FIG. 2, with the same organization as in FIG. 1.

Figure 3:
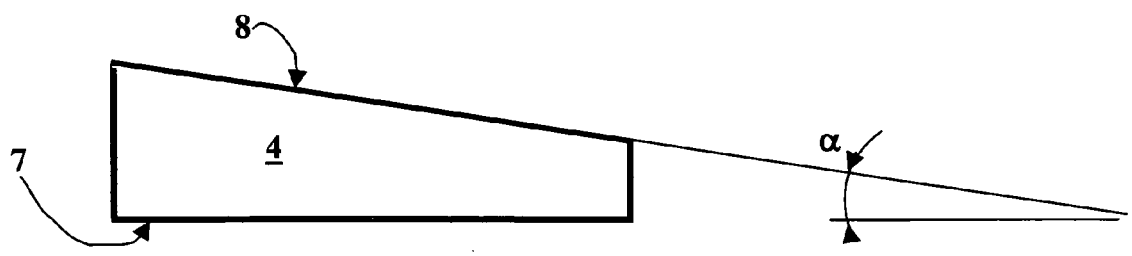
FIG. 3 shows an element of the refractometer.

In FIG. 2, optical element 3 has an interface 8 located between ambient medium 12 and medium 4. The two parts of medium 4 forming interfaces 7 and 8 consist of two planes. These two planes can be parallel as shown in FIG. 2, or form an angle α as shown in FIG. 3.

Photodetector 13 is provided with a glass element 14 in form of a cylinder.

In FIG. 2, light source 1 provided with coding device 2 produces a light ray A. The angle of incidence of light ray A in relation to the normal direction N to interface 8 is α1. At interface 8, ray A is separated into a light ray C reflected in ambient medium 12 and a light ray B refracted in medium 4.

Reflected light ray C forms an angle α3 in relation to the normal direction N to interface 8. According to the reflection phenomenon, angle α3 is equal to angle α1. Photodetector 9 measures the intensity IC of light ray C.

Light ray B forms an angle α2 in relation to the normal direction N to interface 8. Since interface 8 is a plane perpendicular to the plane forming interface 7, light ray B forms an angle α2 in relation to the normal direction N to interface 7. The value of angle α2 is determined by Descartes' light ray refraction laws: $n12.\sin(\alpha1)=n4.\sin(\alpha4)$ with n12 being the refractive index of ambient medium 12 and n4 the refractive index of medium 4. At interface 7, light ray B is separated into a light ray E reflected in medium 4 and a light ray D refracted in medium 5.

Light ray D propagates into medium 5, then enters glass element 14 through a first end. Photodetector 13 measures the intensity ID of light ray D which exits through a second end of glass element 14. Photodetector 13 performs at least three measurements of intensity $ID_1$, $ID_2$ and $ID_3$ of ray D at respectively three distances $d_1$, $d_2$ and $d_3$ (not illustrated) between glass element 14 and interface 7.

Light ray E forms an angle α4 in relation to the normal N to interface 8. According to the reflection phenomenon, angle α4 is equal to angle α2. Light ray E propagates in medium 4, then is refracted at interface 8 in ambient medium 12 with an angle α5 in relation to the normal direction N to interface 8. Since interface 8 is a plane perpendicular to the plane forming interface 7, light ray E forms an angle α4 in relation to the normal direction N to interface 8. The value of angle α5 is determined by Descartes' light ray refraction laws: n4.sin(α4)=n12.sin(α5) with n12 being the refractive index of ambient medium 12 and n4 being the refractive index of medium 4. The intensity IE of light ray E is measured by photodetector 10.

According to the configuration of FIG. 2, angle α3 is equal to angle α5. By choosing the distances that separate the various elements of the refractometer, the location of these elements is defined with precision. When using a medium 4 according to FIG. 3, the angle of inclination of interface 7 in relation to interface 8 has to be taken into account to define the trajectory of the various light rays.

Photodetectors 9 and 10 can be replaced by a single photodetector measuring successively and alternately the intensity IC of light ray C and then intensity IE of light ray E.

The arrangement of the components of the refractometer according to the invention is so selected that the angle of incidence of light ray B in relation to the normal direction N to interface 7 is smaller than the critical angle, if there is one. In fact, according to Fresnel's formulas, the intensity of the reflected light ray E depends on the refractive index of medium 5 for any angle of incidence of light ray B between 0° and the critical angle of total reflection. For an angle of incidence of light ray B larger than the critical angle, the intensity of light ray B can be absorbed in medium 5 because of the evanescent wave phenomenon.

Preferably, the layout of the components of the refractometer according to the invention is so selected that the angle of incidence of light ray B in relation to the normal direction N to interface 7 is below 10°, advantageously below 30 and preferably zero. In fact, the intensity of reflected light ray E depends on the state of polarization of light ray B, except when the angle of incidence of light ray B is small (at least below 100, advantageously below 3° and preferably zero). As a consequence, when using a small angle of incidence of light ray B, the intensity of light ray E is not substantially influenced by the polarization of light ray B, therefore is not substantially influenced by the polarization of the ray emitted by light source 1. This allows increasing the precision and the reliability of the refractive index measurements according to the present invention.

The reflection phenomenon produces on interface 7 a reflected light ray E of an intensity of the order of several percent of the intensity of incident ray B. The optical element 3 is so selected that the intensity IC of light ray C also represents several percent of the intensity IB of light ray B. Thus, signal processor 11 analyzes, by means of photodetectors 9 and 10, rays having comparable intensity values. This is preferable for the electronic amplification and comparison elements of the signal processor 11 and improves the precision of the measurements and of the results.

Coder 2 allows the light ray produced by light source 1 to be provided with recognizable characteristics. The intensity of light ray A can vary periodically, for example by varying sinusoidally at fixed frequencies of about 10 kHz, around a given mean value. Since the sinusoidal variation of the intensity of light ray A is not affected by the effects of optical element 3, or by the reflection and refraction phenomena, the intensities of light rays C, D and E similarly vary sinusoidally at about 10 kHz, but around a different mean value. The signal processor 11 has knowledge of the coding carried out by coder 2 and can distinguish, from among the information provided by detectors 9, 10 and 13, the intensities of light rays C, D and E from the other parasitic signals such as those of the ambient light.

Furthermore, the coder 2 can produce a light ray having square-wave varying in intensity between a light ray of full intensity and a light ray of zero intensity. The square-wave signal can be a full-intensity phase during a time $t_1$ of 1 second, then of a zero-intensity phase during a time $t_2$, for example 2 seconds. The cycle of the succession of times $t_1$ and $t_2$ is repeated throughout the measuring stage. The energy locally absorbed by medium 5 at interface 7 during the full-intensity phase has time to diffuse and dissipate in medium 5 during the zero-intensity phase. Thus, the variation of the refractive index value of medium 5 due to the temperature rise remains low. Coding of the intensity of light ray A in a form of a square-wave signal is particularly suited for measurement of the refractive index of opaque media which absorb light quite rapidly.

Figure 4:
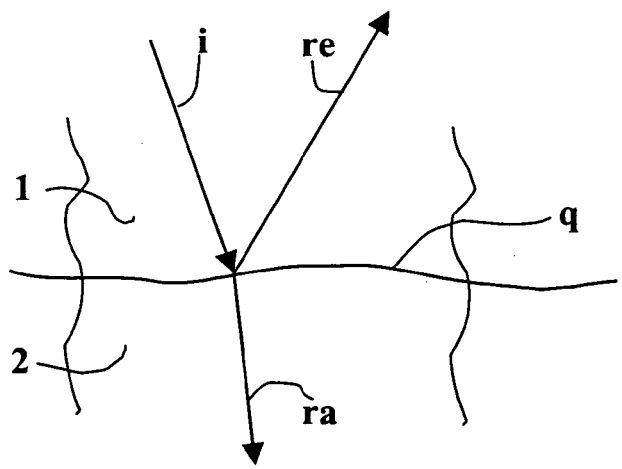
FIG. 4 diagrammatically shows the phenomenon of refraction and reflection of a light ray directed onto an interface.

Reflection of a light ray, which is a phenomenon on which the invention is based, is described in connection with FIG. 4 for example by Fresnel's formulas relating the intensity li of incident ray i to the intensity Ire of reflected light ray re at the level of an interface q as a function of refractive indices n1 and n2 of the two media 1 and 2 forming the interface. Ray ra represents the ray refracted in medium 2. Fresnel's formulas describe the phenomenon of reflection and polarization of the incident light.

Without departing from the scope of the invention, it is possible to use any formula equivalent to Fresnel's formulas describing the reflection phenomenon at an interface from the point of view of the intensities of the incident and reflected rays, by taking into account the refractive indices of the two media forming the interface. When the angle of the incident ray i on interface q is zero, Fresnel's formulas are written in form of a single expression:

$$\frac{I_i}{I_r} = \frac{\left[\left(\frac{n_2}{n_1}\right) - 1\right]^2}{\left[\left(\frac{n_2}{n_1}\right) + 1\right]^2}$$

According to the invention, by measuring the intensity IC of ray C and knowing the distribution of the intensity IA of ray A between rays B and C by means of optical element 3, the intensity IB of ray B is determined. By measuring the intensity IC of ray C to determine the intensity IB of ray B, a more accurate measurement is obtained because the value of intensity IC is comparable to intensity IE.

After determining the intensity IB of light ray B, by measuring the intensity IE of light ray E, and knowing the refractive index n4 of medium 4, the refractive index n5 of the medium studied 5 is determined by means of Fresnel's formulas.

The reflection and refraction phenomena, notably at the level of optical element 3, as ray B passes from medium 12 to medium 4 and ray E passes from medium 4 to medium 12, can be advantageously disregarded because their influence on intensities IB and IE are comparable.

In order to precisely determine, as ray A passes through optical element 3, the value of the ratio of intensity IC of light ray C divided by the intensity IB of light ray B, a medium 5 of known refractive index n5 is placed in the refractometer according to the invention. The intensity IB of light ray B is determined using Fresnel's formulas, knowing the refractive indices n4 and n5 of media 4 and 5 and by measuring the intensity IE of light ray E. Since the intensity IC of light ray C is measured, the ratio of intensity IC to intensity IB is known with precision, the ratio being used for implementing the refractometer according to the invention in order to determine the refractive index of a medium 5. This ratio is known as the "measuring device constant".

The refractive index n of a medium can be written in form of a complex number $n=r+i\cdot\chi$, r being the real part and $\chi$ the imaginary part. Imaginary part $\chi$ describes the phenomenon of absorption of a ray propagating in an opaque medium. While traversing medium 5, the intensity ID of ray D decreases as a function of the distance d travelled from interface 7, according to a law of the form: $ID(d)=k\cdot e^{-\chi\cdot d}$, k being the value of the intensity ID of ray D at interface 7, i.e. for d=0.

Thus, by measuring the intensity ID of ray D at least at a distance d (not illustrated) between photodetector 13 and interface 7, preferably by measuring at least three intensities $ID_1$, $ID_2$ and $ID_3$ at respectively three distances $d_1$, $d_2$ and $d_3$ (not illustrated) between photodetector 13 and interface 7, the imaginary part $\chi5$ of medium 5 can be determined. If photodetector 13 is provided with a glass element, distances d, $d_1$, $d_2$ and $d_3$ correspond to the distance between interface 7 and one end of the glass element.

Measurement of imaginary part $\chi$ characterizes more precisely the medium studied and it notably allows evaluating the absorbent character of the medium studied.

The refractometer according to the invention thus allows determination simultaneously, at a given wavelength, the value of the refractive index and the absorption value of a medium studied.

The invention claimed is:

1. A refractometer comprising a light source, a first interface between a first medium of unknown index and of a second medium of known index and at least one detector measuring intensity of an incident light ray, intensity of a reflected light ray resulting from reflection of the incident light ray on the first interface, a coder which codes light rays emitted by the light source and a decoder of measurements performed by the detector, the decoder exchanging information with the CODER.

2. A refractometer as claimed in claim 1, wherein the first medium is contained in an enclosure comprising a shell and the second medium.

3. A refractometer as claimed in claim 1, comprising an optical element dividing a light ray into two light rays which forms a measuring ray and the incident ray with intensity of the measuring ray being measured by a detector.

4. A refractometer as claimed in claim 3, wherein the optical element is an second interface formed by a surface of the first medium located outside an enclosure.

5. A refractometer as claimed in claim 3, wherein the optical element is a semireflecting blade.

6. A refractometer as claimed in claim 1, comprising a detector which measures intensity of a light ray refracted in the first medium.

7. A refractometer as claimed in claim 1, wherein an angle of incidence of the incident light ray in relation to the normal direction to first interface is smaller than the critical angle.

8. A refractometer as claimed in claim 1, wherein an angle of incidence of the incident light ray in relation to a normal direction to first interface is below 10°.

9. A method of measuring the refractive index of a first medium, comprising the steps of:
   directing an incident light ray onto an interface between a first medium and a second medium of known refractive index so as to produce a reflected light ray;
   measuring intensity of the reference light ray and intensity of the reflected light ray;
   determining the refractive index of the first medium by utilization of at least the refractive index of the second medium, the intensity of the incident light ray and the intensity of the reflected light ray; and wherein
   the intensity of the light ray refracted in the first medium is measured and absorption of the refracted light ray by first medium is determined.

* * * * *